United States Patent
Holcomb

(10) Patent No.: US 7,238,824 B2
(45) Date of Patent: Jul. 3, 2007

(54) DERIVATIZING ORGANOMETALLIC HALIDES

(75) Inventor: Nelson Robert Holcomb, Palo Alto, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 216 days.

(21) Appl. No.: 10/863,715

(22) Filed: Jun. 7, 2004

(65) Prior Publication Data

US 2005/0272946 A1  Dec. 8, 2005

(51) Int. Cl.
*C07F 7/04* (2006.01)
*C07F 7/00* (2006.01)

(52) U.S. Cl. .......................... 556/482; 556/88; 556/89; 556/470

(58) Field of Classification Search ................. 556/88, 556/89, 470, 482
See application file for complete search history.

(56) References Cited

U.S. PATENT DOCUMENTS 3,299,166 A * 1/1967 Emblem et al. .............. 528/27

OTHER PUBLICATIONS

Voronkov et al., Chemical Abstracts, vol. 68, No. 7, abstract No. 29763r (1968).*
Voronkov, M.G., et al. "Nitrogen-containing Organosilicon Compounds", Institute of Organic Synthesis, Acad. of Sci. of the Latvian SSR, Translated from *Zhurnal Obshchei Khimii*, 37:7, pp. 1673-1676 (Jul. 1967).

* cited by examiner

*Primary Examiner*—Porfirio Nazario-Gonzalez

(57) ABSTRACT

Methods, compounds, and kits are provided for derivatizing organometallic halide compounds. The methods include reacting an organometallic halide with a reagent to produce an analyte having desired properties. In a preferred form, the analyte has properties that render it more susceptible to chemical analysis in relation to its respective organometallic halide. The compounds include the analyte product of the derivatization reaction. The kits include a reagent and, preferably, some or all of the tools that may be used to perform the derivatization reaction.

11 Claims, No Drawings

DERIVATIZING ORGANOMETALLIC HALIDES

BACKGROUND

Several methods are known for analyzing chemical compounds, including mass spectrometry (MS), gas or liquid chromatography (GC or LC), and nuclear magnetic resonance imaging (NMR). Each of these methods requires the user to introduce a chemical compound to the apparatus used to perform the chemical analysis. The following is a brief description of these apparatus and methods, which description is not intended to be comprehensive, or to limit in any way the application of the compounds and methods described herein. A more detailed description of these analytical methods may be obtained from the contemporary scientific literature. Moreover, those skilled in the analytical chemistry arts will be familiar with these methods and the apparatus used to perform these methods.

For example, mass spectrometry involves the analysis of ionized analytes in a gas phase using an ion source, a mass analyzer that measures the mass-to-charge (m/z) ratio of the ionized analytes, and a detector that registers the number of ions at each m/z value. The MS apparatus may also be coupled to a separation apparatus to improve the ability to analyze complex mixtures. Further, MS instrument combinations can be made to enhance sensitivity and selectivity. Regarding ion source, electrospray ionization (ESI) and matrix-assisted laser desorption/ionization (MALDI) are two commonly used techniques to ionize the chemical compounds for analysis. ESI ionizes the analytes from a solution and, depending on the ionization method, may result in either negatively or positively charged ions. MALDI desorbs and ionizes the sample using a "matrix" that encourages desorption and ionization when exposed to light energy.

There are several types of mass analyzers, including ion trap, time-of-flight (TOF), quadrupole (Qq) magnetic sector, and Fourier transform ion clyclotron (FT-MS) analyzers, each varying in analysis characteristics. These analyzers may be run separately or assembled in tandem to maximize sensitivity and strengths of MS analysis. For example, MALDI is usually coupled to a TOF analyzer, but may also be coupled to quadrupole ion-trap and to combined TOF instruments or FT-MS. For example, in TOF-TOF, two TOF sections are separated by a collision cell. In the hybrid quadrupole TOF apparatus, the collision cell is placed between a quadrupole mass filter and a TOF analyzer. These examples illustrate how "tandem" mass spectrometry apparatus may be assembled from intact MS apparatus or selected components of the instruments. The design of the tandem MS instrument allows versatility and increased sensitivity depending on the goal of the analysis and the chemical composition of the analyte.

Chromatography involves separation of molecules based on differences in their structure and/or composition. In general, chromatography involves moving a sample of the materials to be separated over a stationary support. The molecules in the sample will have different interactions with the stationary support leading to separation of similar molecules. Test molecules which display tighter interactions with the support will tend to move more slowly through the support than those molecules with weaker interactions. In this way, different types of molecules can be separated from each other as they move over the support material.

Chromatographic separations can be carried out using a variety of supports, including immobilized silica on glass plates (thin layer chromatography), volatile gases (gas chromatography), paper (paper chromatography), and liquids which may incorporate hydrophilic, insoluble molecules (liquid chromatography).

A gas chromatograph includes three major components: an analytical column that physically separates the components of the mixture, a detector that senses the individual component after separation, and an injector that introduces the gas sample and carries the sample to the analytical column by carrier gas.

Nuclear magnetic resonance (NMR) is a physical phenomenon involving the interaction of atomic nuclei placed in an external magnetic field with an applied electromagnetic field oscillating at a particular frequency. Magnetic conditions within the material are measured by monitoring the radiation absorbed and emitted by the atomic nuclei. NMR is used as a spectroscopy technique to obtain physical, chemical, and electronic properties of molecules.

In NMR, the sample to be tested is placed in a static external magnetic field. An antenna (usually a coil-shaped inductor with the sample inside) is used to irradiate the sample with radio waves. At certain frequencies, atomic nuclei within the sample will absorb the radiation and enter an excited state. After a time, the nuclei will re-emit the radiation, which can be detected by the antenna. Finally, a measurement is taken of how much radiation is re-emitted, and when. Only nuclei with non-zero magnetic moment can undergo NMR.

Highly reactive materials, such as organometallic halides, present several problems when attempts are made to perform MS, chromatographic, NMR, or other chemical analyses on them. In particular, these materials are highly reactive to many of the tools currently employed in chemical analysis. For example, many organometallic halides will react rapidly with rubber, glass, and other oxides upon injection into a gas chromatograph, or when used in glass capillaries used in electrospray mass spectrometry, resulting in erroneous analysis results when the instrumental data output is examined.

In addition, many of the organometallic halides will readily hydrolyze when they are placed in an aqueous buffer media, which may be used in electrospray MS, thereby leading to flawed measurement results. These materials may also be difficult to ionize, also leading to difficulties when they are being analyzed using electrospray MS.

One class of organometallic halides—organochloro silanes—is used extensively for surface coatings, to add lubricity, and for other purposes. Organochloro silanes are used, for example, to create hydrophobic coatings for analytical instruments, such as protein arrays, DNA arrays, and gas and liquid chromatograph columns. They are also used as protective coatings on windshields, and as lubricants on magnetic media such as disk drives. For many of these applications, it is useful to perform some chemical analysis, such as MS, LC or GC, or NMR, prior to forming the coatings in order to confirm the identity of the organochloro silane being used.

Therefore, there exists a need for methods and compounds that are useful to facilitate the analysis of organometallic halides by mass spectrometry, gas or liquid chromatography, nuclear magnetic resonance imaging, and other methods that require the use of equipment with which the organometallic halides might react.

SUMMARY OF THE INVENTION

The present invention is a novel approach to chemical derivatization of organometallic halides to facilitate chemical and structural analysis of those materials. The invention includes both methods and compositions of matter and specifically encompasses chemical derivatives, kits for forming such chemical derivatives, methods for forming such chemical derivatives, the use of chemical derivatives in analytic methods including MS, GC and LC, and NMR, and methods, apparatus, and compositions for the use of all of the above.

The benefits of the invention are derived from an improvement in the ability to perform chemical analyses of organometallic halide compounds. The result of this improvement is to provide more accurate results when these compounds are subjected to MS, GC or LC, NMR, or other chemical analyses.

The improvements and advantages of the invention result from derivatizing organometallic halide compounds using chemical reagents that are selected and designed to yield analytes that are less reactive with the apparatus used to perform the chemical analysis. Preferably, these analytes are also less likely to hydrolyze in an aqueous buffer solution than are the organometallic halides, and the analytes are more susceptible to ionization than the organometallic halides in order to facilitate electrospray ionization used in some MS methods.

The organometallic halides that are the subject of the compounds and methods described herein are represented by the following structure:

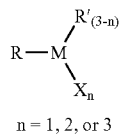

n = 1, 2, or 3 where R and R' are organic groups that may include, without limitation, straight chain alkyls, branched or substituted alkyls, aromatics, cyclics, and other organic moieties. R and R' may or may not be identical. The organic groups R and R' may also contain other functional groups. M represents one of the Group IV metals, preferably either Si, Ge, or Sn, and most preferred, Si. Finally, X represents a halogen, preferably either Cl, Br, or I, and most preferred, Cl.

In several preferred embodiments, the organometallic halides are organochloro silanes having the following structure:

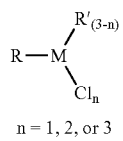

n = 1, 2, or 3

One exemplary group of these materials are the trichlorosilanes:

These materials are used extensively as coatings and lubricants for metal, glass, and other hard surfaces.

In several preferred embodiments, the reagent that is reacted with the organometallic halide to form the analyte is an alcohol having the following structure:

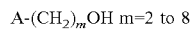

In the foregoing formula, A represents a functional moiety that is selected to provide the desired benefits from the substitution of the substituent on the organometallic halide. A preferred example of the functional moiety A is an amino group ($NH_2$). The preferred substituent alcohol is 2-aminoethanol:

The derivation reaction is preferably a substitution reaction whereby the organometallic halide is reacted with the reagent alcohol to form the modified analyte:

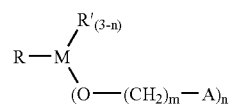

where, once again, n is either 1, 2, or 3, and m is an integer between 2 and 8, inclusive. Because the halide contained on the organometallic halide has been replaced by the alcohol group, the modified analyte is a compound that is far less reactive with glass, rubber, metal, and other materials contained in MS, GC, LC, and NMR instruments. Moreover, depending on the selection of the functional moiety A, the modified analyte may also be substantially less likely to hydrolyze when it is placed in an aqueous buffer or other solution, such as during the formation of a charge in electrospray ionization. Still further, and again, depending on the selection of the functional moiety A, the modified analyte may be more susceptible to ionization during the electrospray ionization process relative to the organometallic halide. In particular, the modified analyte may be more readily ionized using methods that are more gentle than those needed to ionize the organometallic halide, thereby reducing the amount of fragmentation and producing better analytical results.

After derivatization, the modified analyte may be subjected to chemical analysis, such as by MS, GC, LC, or NMR. The analyte comprises a derivatization of the organometallic halide that has been modified to reduce or eliminate its reactivity with the analytical instruments, thereby allowing the user to obtain more accurate results measuring the mass-to-charge ratio, chemical structure, or other properties of the analyte. This information can be used either to confirm the identity of the original organometallic halide, or to determine its identity if a particular organometallic was not suspected.

In a further aspect of the present invention, a kit is provided that contains a reagent used to derivatize an organometallic halide. The kit preferably contains a reaction vessel, such as a glass vial or bottle, which contains the reagent. A solvent is preferably also included, either in a separate container or in the same container with the reagent. Depending on the identities of the organometallic halide and the reagent, the kit may also be provided with a venting means to be used for the derivatization reaction, such as a small needle that provides access to the reaction vessel. Any of the reagents discussed above may be provided with the kit, and the choice of reagent may depend on the organometallic halide being analyzed.

DESCRIPTION OF THE SPECIFIC EMBODIMENTS

Methods for derivatizing organometallic halides to create analytes having improved susceptibility to chemical analysis, compounds produced thereby, and kits used to perform the derivatization, are provided. In the subject methods, organometallic halides are reacted with a reagent to provide an analyte. One of the benefits that may be obtained from the derivatization is a reduction of the reactivity of the organometallic halide to provide an analyte that is more susceptible to analysis by MS, GC, LC, or NMR. Another benefit that may be obtained from the derivatization is to obtain an analyte having greater stability in a buffer solution—such as those used in electrospray ionization—relative to the stability of the organometallic halide. Yet another benefit that may be obtained from the derivatization is to obtain an analyte that is more susceptible to ionization, or that is susceptible to ionization by more gentle methods that would be the case with the organometallic halide.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

1. Organometallic Halides

As summarized above, the subject invention provides methods for derivatizing organometallic halides. The subject organometallic halides have the following chemical structure:

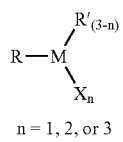

n = 1, 2, or 3

In this formula, R and R' are organic groups that may include, without limitation, straight chain alkyls, branched or substituted alkyls, aromatics, cyclics, and other organic moieties. R and R' may or may not be identical. For example, and not for the purpose of limitation, R may be a long chain aliphatic group (e.g., dodecyl, decyl, octyl, etc.), a branched aliphatic group (e.g., isooctane, etc.), or an unsaturated aliphatic substituent (e.g., alkylbenzyl, olefinic, or other unsaturated materials), while R' may be a short aliphatic chain or heteroatomic chemical substituent (e.g., ethyl, methyl, isopropyl, cyanoethyl, etc.). The organic groups R and R' may also contain other functional groups. M represents one of the Group IV metals, preferably either Si, Ge, or Sn. Finally, X represents a halogen, preferably either Cl, Br, or I.

Of the compounds included in the above definitions, those containing Si as the metal and Cl as the halogen are generally more common in industry, and will be a primary focus of the detailed description contained herein. It is to be understood, however, that the methods and compounds described are applicable to the other Group IV metals and halides described herein. In particular, this detailed description is for the purpose of describing particular embodiments, and is not intended to be limiting. Instead, the scope of the present invention will be established by the appended claims.

The organometallic halide compounds containing Si and Cl may be characterized by the following chemical structure:

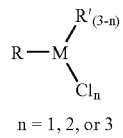

n = 1, 2, or 3

These compounds, organochlorosilanes, are used extensively to provide coatings for metal, glass, and other hard surfaces because the terminal Cl atoms are highly reactive with these surfaces and provide excellent covalent bonding to adhere the molecule to the surface. For these reasons, these materials are used extensively in applications such as DNA or protein arrays, coatings for GC columns, windshield coatings, boundary layer lubricants, coatings on disk drive surfaces, and other applications.

One exemplary group of these materials is the trichlorosilanes:

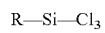

The trichlorosilane molecule contains three terminal Cl atoms attached to the Si atom. It is highly reactive with rubber, glass, and other oxides upon exposure to those materials. As a result, conventional methods of chemical analysis, such as MS, GC, LC, and NMR are not readily usable with these materials or, at best, may provide questionable results. In particular, these trichlorosilanes will readily react with glass used in capillaries used in electrospray mass spectrometry, or with the rubber o-rings used in gas chromatograph injection ports.

2. Reagents

The reagent used to derivatize the organometallic halide is selected or created to produce an analyte from the derivatization reaction that provides one or more of the benefits obtained by the methods and compounds described herein. For example, the reagent is reacted with an organometallic halide to produce an analyte. One of the benefits that may be obtained from the described methods and compounds is to provide an analyte that is, in comparison to the subject organometallic halide, less reactive with the equipment and instruments used to perform chemical analyses, such as MS, GC, LC, or NMR, in order to obtain improved analytical results from those methods. Another benefit that may be obtained from the methods and compounds is to obtain an analyte that is, in comparison to the organometallic halide, more stable in solution with an aqueous buffer, such as those used in electrospray MS. Yet another benefit that may be obtained from the methods and compounds is to obtain an analyte that is, in comparison to the organometallic halide, more susceptible to ionization, or that may be ionized by more gentle methods.

In a preferred form, the reagent will comprise a first moiety that will readily participate in a substitution reaction with the halide component of the organometallic halide, and a second moiety that provides useful functionality to the analyte formed form the derivatization. Thus, the reagent may be characterized as:

Sub—Func where "Sub" represents the substitution reaction moiety and "Func" represents the functionality moiety.

Examples of the "Sub" moiety include relatively short chain-length alcohols, and other functional groups that will readily participate in the substitution reaction with the terminal halide(s) of the organometallic halide. Alcohols are preferred because they are stable, inexpensive, and effective. In particular, alcohols do not diminish the function of the silane, i.e., coating processes, but simply reduce the reactivity of the silanes so that one can carry out an analysis without having the material react with the analytical apparatus. While longer chain alcohols may adequately perform the required substitution reaction, the resultant product will include an increased number of isomers, which is an undesirable result. In a particularly preferred embodiment, the "Sub" moiety is provided by an alcohol group, $C_nH_{2n}$—OH, where n is an integer between 2 and 8, inclusive. The preferred "Sub" moiety is an ethanol group, $C_2H_4$—OH.

Examples of the "Func" moiety include amino groups and other functional groups that will add desired functionality to the analyte that is the product of the derivatization. One such desirable functionality is to have the analyte be easily protonated using relatively gentle ionization methods. For this purpose, an amino group —$NH_2$— is a preferred "Func" moiety.

Thus, a particularly preferred reagent is 2-amino-ethanol:

3. Derivatization of Organometallic Halides

The derivatization that is the subject of the methods and compounds described herein is a reaction of an organometallic halide with a reagent, as those materials are summarized above, to produce an analyte. Thus, the derivatization may be characterized as follows:

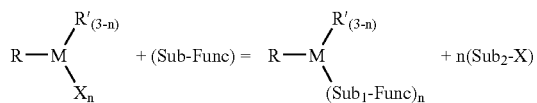

where $Sub_1$ represents the portion of the substitution moiety that bonds to the metal and displaces the halide contained in the organometallic halide, and $Sub_2$ represents the portion of the substitution moiety that bonds to the disassociated halide.

As summarized above, this derivatization has wide application to each of the compounds represented in the above equation. For illustrative purposes, however, the following description pertains to a single preferred embodiment of the derivatization reaction, involving individual species of the compounds represented in the general equation above. In this preferred embodiment, the organometallic halide is Trichloro-decyl-silane:

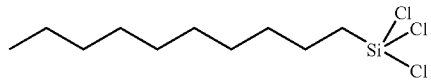

Trichloro-decyl-silane
$C_{10}H_{21}Cl_3Si$
Exact Mass: 274.05
Mol. Wt.: 275.72

The reagent used in this preferred embodiment is 2-amino-ethanol:

$H_2N$—$(CH_2)_2$—OH $C_2H_7NO$

Exact Mass: 61.05

Mol. Wt.: 61.08

The analyte produced by the derivatization of these two materials is Tris(2-aminoethoxy)-decyl-silane:

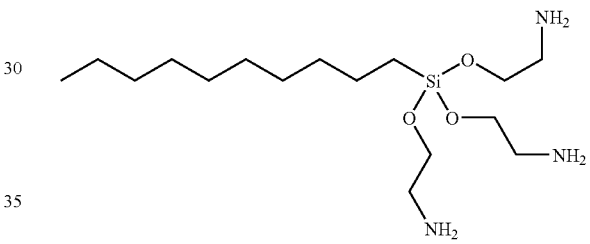

Tris(2-aminoethoxy)-decyl-silane
$C_{18}H_{39}N_3O_3Si$
Exact Mass: 349.28
Mol. Wt.: 349.58

The derivatization of trichloro-decyl-silane by 2-amino-ethanol may be achieved by the following method. In a clean 1–2 ml glass vial add 1 ml toluene and 120 ml 2-aminoethanol and seal the vial with a septum screw cap or septum crimp cap. Stir or shake the mixture for 5 minutes to mix well and dissolve the 2-amino-ethanol in the toluene solvent. Place a small needle into the vial and slowly add 95 ul of trichloro-decyl-silane to the glass vial with a microliter syringe while agitating the solution. HCl gas will be emitted and must be allowed to escape via the small needle. It is important not to block the needle, or to immerse or splash solution onto the needle during agitation. The reaction product, Tris(2-aminoethoxy)-decyl-silane, will typically precipitate to the bottom of the vial as a white powder or become gelatinous. After addition of the trichloro-decyl-silane, agitate for an additional 10 minutes, then remove the vent and place the vial in a hood. If the precipitate appears in the vial and it does not appear to go into solution, place the vial in a warm oven (approximately 50° C.) for one hour to allow the derivatization reaction to complete. Once the reaction is complete, the analyte requires no additional purification or any other chemical or physical preparation prior to performing a chemical analysis upon it. The derivatization reaction is represented below:

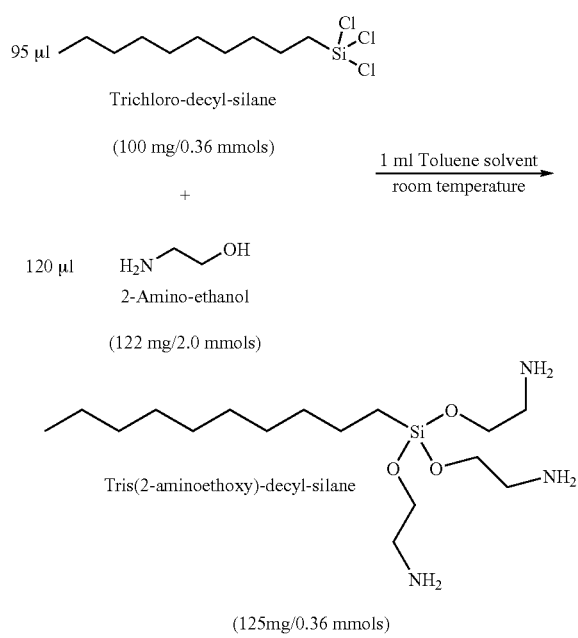

The derivatization preferably takes place in the presence of a solvent, and toluene is used as a solvent in the foregoing example. Other solvents may be used. It is preferable to conduct the reaction in a non-polar organic solvent selected such that the organometallic molecule of interest is soluble in the solvent and the derivatized material has a very low solubility. Other solvents of interest include dimethylformamide (DMF), tetrahydrofuran (THF), and other polar aprotic solvents where the starting reactants are soluble along with the products. The preferred method (using non-polar solvents, like toluene) results in a precipitation of the products of the reaction, thus simplifying the analysis by separating spontaneously.

The modification of tricholorosilanes described above provides several benefits. For example, it reduces the reactivity of the silanes toward the tools used to analyze them, e.g., the glass used in the capillaries used in electrospray MS, or the rubber o-rings used in gas chromatograph injection ports. Moreover, this modification slows the hydrolysis of the silanes to a level sufficient so that aqueous buffer media may be used to facilitate the formation of a charge in electrospray, i.e., use of an HCN containing buffer is made possible by this modification. Still further, this modification creates the ability to protonate the resulting silane using more gentle ionization methods than electrical ionization. Other and further benefits will be observed and understood by a person of skill in the art practicing the methods described herein.

As noted herein, the derivatization of trichloro-decyl-silane by 2-amino-ethanol is described here solely for purposes of illustration of the methods and compounds described more broadly above. Derivatizations of others of the organometallic halides described above by others of the reagents described above may be achieved using the same or similar methods to those described in this section and elsewhere. For example, germanium and tin organo-halide compounds may be derivatized using 2-amino-ethanol or other reagents utilizing methodology similar to that described above to provide analytes based on those compounds, which analytes would provide the same benefits as those described in relation to the tricholoro-silane compounds.

4. Kits for Performing Derivatizations of Organometallic Halides

A kit may be provided having a reagent and some or all of the tools needed to perform a derivatization of an organometallic halide. The reagent contained in the kit is selected according to the identity or suspected identities of the organometallic halide compound. For example, where the organometallic halide compound under consideration is trichloro-decyl-silane, it is advantageous to provide a kit having 2-amino-ethanol as the reagent. Other combinations of reagent and organometallic halides are also possible, as summarized above.

The kit may contain a quantity of solvent. The solvent and reagent may be contained in a single container, or in separate containers. The kit may also include a reaction vessel, such as a vial, glass, bottle, or other container. Finally, the kit may also contain a venting member, such as a needle, and a measuring tool such as a microliter syringe.

The kit may be used in connection with a chemical analysis of the reaction product obtained from the derivatization. Using the example listed above, a derivatization of trichloro-decyl-silane by 2-amino-ethanol may be performed using the kit, and following the procedure set forth in the preceding section. Once the derivatization reaction is completed, the reaction product may be used as an analyte in a chemical analysis, such as an electrospray ionization mass spectrometry analysis (ESI-MS). The analyte is injected into the electrospray apparatus is protonated, and is then received within the MS instrument where a mass spectrometry analysis is performed. If the original organometallic halide compound was the trichloro-decyl-silane, the results of the MS analysis will indicate the presence of tris(2-aminoethoxy)-decyl-silane, thereby confirming the identity of the original organometallic halide.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the claims.

What is claimed is:

1. A method for derivatizing an organometallic halide compound comprising:
    contacting the organometallic halide compound with a reagent compound, said organometallic halide compound having the formula:

R—Si—Cl$_3$ wherein R is an organic groups,
    and wherein said reagent compound has the formula H$_2$N—(CH$_2$)$_m$—OH, wherein m is an integer between 2 and 8, inclusive.

2. The method of claim 1, wherein said reagent compound has the formula H$_2$N—(CH$_2$)$_2$—OH.

3. The method of claim 1, wherein said contacting step takes place in the presence of toluene as a solvent.

4. A method for performing chemical analysis of an organometallic compound comprising:
    derivatizing said organometallic compound by the method of claim 1 to obtain an analyte, and
    performing a chemical analysis of said analyte.

5. A method for performing chemical analysis of an organometallic compound comprising:

derivatizing said organometallic compound by the method of claim 2 to obtain an analyte, and performing a chemical analysis of said analyte.

6. The method of claim 4, wherein said chemical analysis comprises performing one or more of the analytical methods of the group consisting of mass spectrometry, gas chromatography, liquid chromatography, and nuclear magnetic resonance analysis.

7. The method of claim 6, further comprising the step of:

using the results obtained from the chemical analysis of said analyte to confirm the identity of said organometallic halide compound.

8. The method of claim 6, further comprising the step of:

using the results obtained from the chemical analysis of said analyte to determine the identity of said organometallic halide compound.

9. A kit for derivatizing an organometallic compound comprising:

a first container containing a reagent having the formula $H_2N-(CH_2)_2-OH$, where n is an integer between 2 and 8, inclusive;

a solvent; and the kit further comprising instructions for performing the following method for derivatizing an organometallic halide compound, wherein the instructions comprise:

contacting the organometallic halide compound with a reagent compound, said organometallic halide compound having the formula:

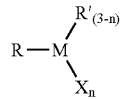

wherein R and R' are organic groups,

M is selected from the group consisting of silicon (Si), germanium (Ge), and tin (Sn), X is selected from the group consisting of chlorine (Cl), bromine (Br), and iodine (I), and n is either 1, 2, or 3;

and wherein said reagent compound has the formula $H_2N-(CH_2)_m-OH$, wherein m is an integer between 2 and 8, inclusive.

10. The kit of claim 9, wherein said solvent is contained in a second container.

11. The kit of claim 9, wherein said solvent is selected from the group consisting of toluene, dimethylformamide (DMF), and tetrahydrofuran (THF).

* * * * *